United States Patent [19]

Kobrehel et al.

[11] Patent Number: 4,517,359

[45] Date of Patent: May 14, 1985

[54] 11-METHYL-11-AZA-4-0-CLADINOSYL-6-0-DESOSAMINYL-15-ETHYL-7,13,14-TRIHYDROXY-3,5,7,9,12,14-HEXAMETHYL-OXACYCLOPENTADECANE-2-ONE AND DERIVATIVES THEREOF

[75] Inventors: Gabrijela Kobrehel; Slobodan Djokic, both of Zagreb, Yugoslavia

[73] Assignee: Sour Pliva farmaceutska, kemijska prehrambena i kozmeticka industrija, n.sol.o., Zagreb, Yugoslavia

[21] Appl. No.: 304,481

[22] Filed: Sep. 22, 1981

[30] Foreign Application Priority Data

Mar. 6, 1981 [YU] Yugoslavia ............................ 592/81

[51] Int. Cl.$^3$ ............................................ C07H 17/08
[52] U.S. Cl. .................................................... 536/7.4
[58] Field of Search ..................... 536/9, 7.4

[56] References Cited

U.S. PATENT DOCUMENTS 4,283,527  8/1981  Sciavolino ........................... 536/7.4
4,328,334  5/1982  Kobrehel et al. .................... 536/7.4

Primary Examiner—Nicky Chan
Attorney, Agent, or Firm—Pollock, Vande Sande & Priddy

[57] ABSTRACT

11-Methyl-11-aza-4-0-cladinosyl-6-0-desosaminyl-15-ethyl-7,13,14-trihydroxy-3,5,7,9,12,14-hexamethyl-oxacyclopentadecane-2-one and derivatives thereof, such as the 13,14-carbonate and $C_1$–$C_3$-alkanoyl derivatives thereof. The compounds exhibit antibacterial activity.

1 Claim, No Drawings

11-METHYL-11-AZA-4-0-CLADINOSYL-6-0-DESOSAMINYL-15-ETHYL-7,13,14-TRIHYDROXY-3,5,7,9,12,14-HEXAMETHYL-OXACYCLOPENTA-DECANE-2-ONE AND DERIVATIVES THEREOF

The present invention relates to new erythromycin A compounds, a process for the manufacture thereof and to the use of new erythromycin A (11-methyl-11-aza-4-0-cladinosyl-6-0-desosaminyl-15-ethyl-7,13,14-trihydroxy-3,5,7,9,12,14-hexamethyloxacyclopentadecane-2-one) compounds in the control of bacteria.

The new compounds, namely N-methyl-11-aza-10-deoxo-10-dihydroerythromycin A and derivatives thereof, are characterized by the general formula

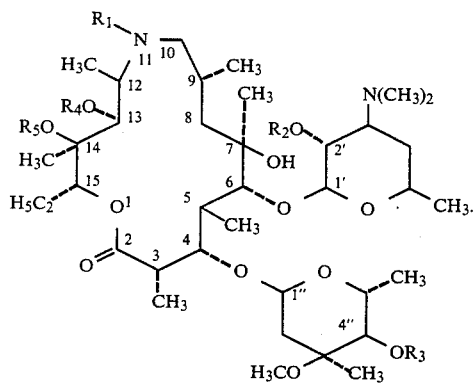

wherein $R_1$ stands for methyl, whereas $R_2$, $R_3$, $R_4$ and $R_5$, which may have equal or different meanings, stand for hydrogen atoms, $C_1$–$C_3$-alkanoyl groups or $R_4$ and $R_5$ together form a >C=O group, and exhibit antibacterial activity. When at least one of $R_3$ and $R_4$ is a $C_1$–$C_3$ alkanoyl group, $R_2$ is other than hydrogen.

It has been known that ammonia, primary and secondary amines may be reductively alkylated by means of aldehydes and ketones resp., yielding tertiary amines (Org. Reactions 4, 174–225, 1948; Org. Reactions 5, 301, 1949; J. Org. Chem. 37, 1673, 1972; Synthesis 55, 1974).

It has been known as well that the methylation of primary and secondary amines is mostly performed according to the Eschweil-Clark method, namely by the reaction of an amine with formaldehyde in the presence of formic acid (Ber. 38, 880–882, 1905; J. Amer. Chem. Soc. 55, 4571–4587, 1933; The Acydic Aliphatic Tertiary Amines, pp. 44–52, The Macmillan Company, New York 1965).

It has further been known that Beckmann's rearrangement of erythromycin A oxime, followed by the reduction of the obtained product, yields a 15-membered semisynthetic antibiotic of the erythromycin series, i.e. 11-aza-10-deoxo-10-dihydro erythromycin A (German Offenlegungsschrift 30 12 533).

It has also been known that the reaction of erythromycin A with ethylene carbonate yields an 11,12-cyclic carbonate of erythromycin A, which is one of those rare erythromycin derivatives that exhibit an improved antibacterial activity if compared with the starting antibiotic (U.S. Pat. No. 3,417,077; Rocz. Chem. 46, 2212–2217, 1972).

It has now been found that N-methyl-11-aza-10-deoxo-10-dihydro erythromycin A of the above-defined formula (1), wherein $R_1$ stands for methyl, whereas $R_2$, $R_3$, $R_4$ and $R_5$ are hydrogen atoms, may be obtained by the reaction of 11-aza-10-deoxo-10-dihydro erythromycin A of the formula (1), wherein $R_1$, $R_2$, $R_3$, $R_4$ and $R_5$ are identical and stand for hydrogen atoms, with formaldehyde in the presence of formic acid.

The present inventive methylation of 11-aza-10-deoxo-10-dihydro erythromycin A is most suitably performed with a 1–3 molar excess of formaldehyde and formic acid in an appropriate solvent, preferably in a halogenated hydrocarbon, e.g. chloroform or carbon tetrachloride. The reaction is complete in 2 to 8 hours while refluxing. The reaction product is isolated in a conventional manner, most suitably by cooling to ambient temperature, addition of water, adjusting the pH value to about 5.0 by means of 2N HCl, separation of the solvent and extraction of the aqueous layer with the same solvent, subsequently to the adjustment of the pH value to about 7.5 by means of 20% w./w. NaOH. The combined organic extracts are dried over $K_2CO_3$ and evaporated under reduced pressure, yielding a chromatographically pure N-methyl-11-ara-10-deoxo-10-dihydroerythromycin A (elution with dimethylformamide:methanol = 3:1).

It has also been established that the reaction of the above obtained N-methyl-11-aza-10-deoxo-10-dihydro erythromycin A with a 1–6 molar excess of ethylene carbonate in the presence of an alkali, e.g. $K_2CO_3$, in an appropriate inert organic solvent, e.g. benzene or ethyl acetate, at a temperature of about 60° to 80° C. during 1 to 8 hours yield a 13,14-cyclic carbonate of N-methyl-11-aza-10-deoxo-10-dihydro erythromycin A. The product may be isolated in a conventional manner, most suitably by washing the organic solution with water and drying over $CaCl_2$.

The reaction of N-methyl-11-aza-10-deoxo-10-dihydro erythromycin A and its 13,14-cyclic carbonates with carboxylic acid anhydrides of the formula $$R_6—O—R_7 \quad (2)$$

wherein $R_6$ and $R_7$ correspond to the meanings of $R_2$ and $R_3$ resp. or $R_4$ and $R_5$ resp., with the provision that they stand for $C_1$–$C_3$ alkanoyl groups, yields the corresponding acyl derivatives of the formula (1), wherein $R_1$ stands for a methyl groups, $R_2$ for a $C_1$–$C_3$ alkanoyl group, $R_3$ for a hydrogen atom or a $C_1$–$C_3$ alkanoyl group, $R_4$ for a hydrogen atom, a $C_1$–$C_3$ alkanoyl group, or $R_4$ and $R_5$ together form a >C=O group, whereas $R_5$ stands for a hydrogen atom or together with $R_4$ stands for a >C=O group. The reaction is carried out in pyridine at a temperature of about ambient temperature to about 80° C. When heating, a $N_2$ atmosphere should be applied. The resulting product is isolated by conventional extraction methods (J. Med. Chem. 15, 631, 1972).

The new compounds were tested in vitro on a series of test microorganisms. The results are shown in Tables 1 and 2 as Minimum Inhibitory Concentrations (MIC) in comparison with the starting 11-aza-10-deoxo-10-dihydro erythromycin A. The antibacterial activity of the novel compounds substantially corresponds to that of the control substance, yet N-methyl-11-aza-10-deoxo-10-dihydro erythromycin A and its derivatives exhibit a superior effect on some tested microorganisms with respect to the starting 11-aza-10-deoxo-10-dihydroerythromycin A.

TABLE 1

Minimum Inhibitory Concentrations (MIC)

| Test strains | Results expressed in mcg/ml | | | | | |
|---|---|---|---|---|---|---|
| | Standard | 1 | 2 | 3 | 5 | 6+ |
| *Streptococcus faecalis* ATCC 8043 | 0.05 | 0.01 | 0.1 | 0.5 | 0.05 | 0.1 |
| *Staphylococcus epidermidis* ATCC 12228 | 0.5 | 0.5 | 0.5 | 2.5 | 0.05 | 0.1 |
| *Staphylococcus aureus* ATCC 6538-P | 0.5 | 0.5 | 0.5 | 0.5 | 0.1 | 0.5 |
| *Micrococcus flavus* ATCC 10240 | 0.05 | 0.01 | 0.5 | 0.1 | 0.05 | 0.5 |
| *Sarcina lutea* ATCC 9341 | 0.05 | 0.05 | 0.1 | 0.1 | 0.05 | 0.05 |
| *Bacillus cereus* var. *mycoides* ATCC 11778 | 0.5 | 0.5 | 0.5 | 0.5 | 0.5 | 0.5 |
| *Bacillus subtilis* ATCC 6633 | 0.5 | 0.1 | 0.1 | 2.5 | 0.5 | 0.1 |

Standard: 11-aza-10-deoxo-10-dihydro erythromycin A
1 = N—methyl-11-aza-10-deoxo-10-dihydro erythromycin A
2 = 2'-acetyl-N—methyl-11-aza-10-deoxo-10-dihydro erythromycin A
3 = 2',4''-diacetyl-N—methyl-11-aza-10-deoxo-10-dihydro erythromycin A
5 = 2'-propionyl-N—methyl-11-aza-10-deoxo-10-dihydro erythromycin A
6 = 2',4''-dipropionyl-N—methyl-11-aza-10-deoxo-10-dihydro erythromycin A
+The Arabic figures correspond to the notation of the Examples.
[The compound of Example 4 did not exhibit any satisfactory activity in the above test.]

TABLE 2

Minimum Inhibitory Concentrations (MIC)

| Test strains | Results expressed in mcg/ml | | | | |
|---|---|---|---|---|---|
| | 7 | 8 | 9 | 10 | 11+ |
| *Streptococcus faecalis* ATCC 8043 | 0.05 | 0.05 | 0.5 | 0.1 | 0.1 |
| *Staphylococcus epidermidis* ATCC 12228 | 0.5 | 0.5 | 2.5 | 0.5 | 2.5 |
| *Staphylococcus aureus* ATCC 6538-P | 0.1 | 0.1 | 2.5 | 0.5 | 2.5 |
| *Micrococcus flavus* ATCC 10240 | 0.1 | 0.1 | 1.0 | 0.5 | 0.5 |
| *Sarcina lutea* ATCC 9341 | 0.1 | 0.05 | 0.1 | 0.05 | 0.05 |
| *Bacillus cereus* var. *mycoides* ATCC 11778 | 0.1 | 0.1 | 2.5 | 0.5 | 1.0 |
| *Bacillus subtilis* ATCC 6633 | 0.1 | 0.1 | 2.5 | 1.0 | 1.0 |

7 = N—methyl-11-aza-10-deoxo-10-dihydro erythromycin A 13,14-cyclic carbonate
8 = 2'-acetyl-N—methyl-11-aza-10-deoxo-10-dihydro erythromycin A 13,14-cyclic carbonate
9 = 2',4''-diacetyl-N—methyl-11-aza-10-deoxo-10-dihydro erythromycin A 13,14-cyclic carbonate
10 = 2'-propionyl-N—methyl-11-aza-10-deoxo-10-dihydro erythromycin A 13,14-cyclic carbonate
11 = 2',4''-dipropionyl-N—methyl-11-aza-10-deoxo-10-dihydro erythromycin A 13,14-cyclic carbonate
+The Arabic figures correspond to the notation of the Examples.

The invention is illustrated but in no way limited by the following Examples.

EXAMPLE 1

N-methyl-11-aza-10-deoxo-10-dihydro erythromycin A

To a solution of 0.54 g (0.000722 mole) of 11-aza-10-deoxo-10-dihydro erythromycin A in 20 ml of CHCl$_3$ there were added, while stirring, 0.0589 ml (0.000741 mole) of formaldehyde (approx. 35% w./w.) and 0.0283 g (0.000735 mole) of formic acid (approx. 98 to 100% w./w.). The reaction mixture was stirred for 8 hours while heating under reflux, then cooled to ambient temperature, whereupon there were added 15 ml of water (pH 5.8). The pH of the reaction mixture was adjusted to 5.0 by means of 2N HCl, whereupon the chloroform layer was separated. To the aqueous part there was added 15 ml of CHCl$_3$, the pH of the reaction suspension was adjusted to 7.5 by means of 20% w./w. of NaOH, the layers were separated and subsequently the aqueous layer was extracted three times with 15 ml of CHCl$_3$. The combined chloroform extracts having a pH of 7.5 were dried over K$_2$CO$_3$ and evaporated under reduced pressure, yielding 0.45 g (82.4%) of N-methyl-11-aza-10-deoxo-10-dihydro erythromycin A, m.p. 113°–115° C.

$[\alpha]_D^{20} = -37.0$ (1% in CHCl$_3$); $M^{30} = 748$.

EXAMPLE 2

2'-acetyl-N-methyl-11-aza-10-deoxo-10-dihydro erythromycin A

To a solution of 1.5 g (0.002 mole) of N-methyl-11-aza-10-deoxo-10-dihydro erythromycin A in 40 ml of pyridine there were added 5 ml (0.053 mole) of acetanhydride and it was kept for 90 minutes at ambient temperature. The reaction was stopped by the addition of approx. 50 cm$^3$ of ice and 30 ml of CHCl$_3$, whereupon the pH of the reaction mixture was adjusted to 8.3 by means of 20% w./w. NaOH. The chloroform layer was separated and the aqueous layer was twice re-extracted with 30 ml of CHCl$_3$. The combined chloroform extracts were washed with water (2×50 ml), the chloroform was dried over K$_2$CO$_3$ and subsequently evaporated under reduced pressure, yielding 1.5 g (94.6%) of the crude 2'-acetyl-N-methyl-11-aza-10-deoxo-10-dihydro erythromycin A, m.p. 110°–113° C. Prior to the analysis the product was purified on a silica gel column, system chloroform:methanol=9:1. The chromatographically pure product (chloroform:methanol 7:3) exhibited the following physical constants:

M.p. = 118°–124° C.

IR(CHCl$_3$): 1745 cm$^{-1}$ (C=O ester), 1730 cm$^{-1}$ (C=O lactone) and 1240 cm$^{-1}$ (—C—O— acetate)

$^1$H NMR (CDCl$_3$): 3.33 (3H)s, 2.26 (3H)s, 2.25 (6H)s, 1.99 (3H)s ppm.

EXAMPLE 3

2',4''-diacetyl-N-methyl-11-aza-10-deoxo-10-dihydro erythromycin A

To a solution of 1.5 g (0.002 mole) of N-methyl-11-aza-10-deoxo-10-dihydro erythromycin A in 40 ml of pyridine there were added 10 ml (0.106 mole) of acetanhydride, whereupon it was kept for 7 days at room temperature. The reaction was stopped by the addition of approx. 50 cm$^3$ of ice, whereupon the product was isolated as indicated in Example 2. The crude 2',4''-diacetate (1.52 g, 89.9%) was dissolved while heating in n-hexane, the insoluble matter was filtered off and the filtrate was left to crystallize in an ice-bath. There was obtained analytically pure diacetate, m.p. 98°–102° C.

IR(CHCl$_3$): 1745 cm$^{-1}$ (C=O ester), 1730 cm$^{-1}$ (C=O lactone) and 1240 cm$^{-1}$ (—C—O— acetate)

$^1$H NMR (CDCl$_3$): 3.26 (3H)s, 2.23 (6H)s, 2.10 (3H)s, 2.06 (3H)s, 1.98 (3H)s ppm.

EXAMPLE 4

2',4''-13-triacetyl-N-methyl-11-aza-10-deoxo-10-dihydro erythromycin A

To a solution of 1.5 g (0.002 mole) of N-methyl-11-aza-10-deoxo-10-dihydro erythromycin A in 20 ml of pyridine there were added 10 ml (0.106 mole) of acetanhydride and it was stirred in a N$_2$-stream for 36 hours while heating at 60° to 80° C. The reaction was stopped by the addition of approx. 100 cm$^3$ of ice and the product was isolated by the extraction with chloroform (4×30 ml) at a pH of 8.5. The combined chloroform extracts were washed with a 5% w./w. NaHCO₃ solution (2×50 ml) and dried over K₂CO₃. Subsequently to the evaporation of chloroform the residual precipitate was dried with benzene, whereupon it was purified by chromatography on a silica gel column, system chloroform:methanol=9:1. There were obtained 0.89 g (51%) of analytically pure triacetate.

M.p.=126°–130° C.

IR(CHCl₃): 1738 cm⁻¹ (C=O ester, lactone), 1245 cm⁻¹ (—C—O— acetate)

¹H NMR (CDCl₃): 3.28 (3H)s, 2.29 (6H)s, 2.13 (3H)s, 2.20 (3H)s, 2.03 (3H)s.

EXAMPLE 5

2'-propionyl-N-methyl-11-aza-10-dihydro erythromycin A

To a solution of 0.7 g (0.00094 mole) of N-methyl-11-aza-10-deoxo-10-dihydro erythromycin A in 20 ml of pyridine there were added 6 ml (0.046 mole) of propionic acid anhydride and it was kept for 1 hour at ambient temperature. The reaction was stopped by the addition of ice and the product was isolated by the extraction with chloroform at pH of 8.6 as indicated in Example 2. The crude 2'-monopropionate (0.73 g; 97.3%) was suspended in ether, the insoluble precipitate was filtered off and repeatedly dissolved in 40 ml of CH₂Cl₂, the dichloromethane solution was concentrated by evaporation under reduced pressure to one third of its volume, which result in the crystallization of the analytically pure 2'-propionyl-N-methyl-11-aza-10-deoxo-10-dihydro erythromycin A.

M.p.=164°–166° C.

IR(CHCl₃): 1730 cm⁻¹ (C=O ester and lactone), 1180 cm⁻¹ (—C—O— propionate).

EXAMPLE 6

2',4''-dipropionyl-N-methyl-11-aza-10-deoxo-10-dihydro erythromycin

To a solution of 0.7 g (0.00094 mole) of N-methyl-11-aza-10-deoxo-10-dihydro erythromycin A in 20 ml pyridine there were added 20 ml of propionic acid anhydride (0.155 mole) and it was kept for 7 days at ambient temperature. The reaction was stopped by the addition of ice and the product was isolated as indicated in Example 2. Yield: 0.72 g (89.4%). The chromatography on a silica gel column, system chloroform:methanol=7:3, yielded an analytically pure product, m.p. 80°–83° C.

EXAMPLE 7

N-methyl-11-aza-10-deoxo-10-dihydro erythromycin A 13,14-cyclic carbonate

To a solution of 1.5 g (0.002 mole) of N-methyl-11-aza-10-deoxo-10-dihydro erythromycin A in 30 ml of dry benzene there were added, while stirring, 1 g (0.007 mole) of K₂CO₃ and 1 g (0.011 mole) of ethylene carbonate. The reaction mixture was stirred, while heating under reflux, for 3 hours, cooled to ambient temperature, the benzene solution was washed with water (3×30 ml) and dried over CaCl₂. The evaporation of benzene yielded 1.37 g (88.38%) of crude N-methyl-11-aza-10-deoxo-10-dihydro erythromycin A 13,14-cyclic carbonate, which was, prior to the analysis, purified by chromatography on a silica gel column, system chloroform:methanol=7:3. M.p.=115°–119° C.

$[\alpha]_D^{20} = -31°$ (1% w./w. solution in CHCl₃)

IR(CHCl₃): 1805 cm⁻¹ (C=O carbonate) and 1740 cm⁻¹ (C=O lactone).

EXAMPLE 8

2'-acetyl-N-methyl-11-aza-10-deoxo-10-dihydro erythromycin A 13,14-cyclic carbonate To a solution of 1 g (0.0013 mole) of N-methyl-11-aza-10-deoxo-10-dihydro erythromycin A 13,14-cyclic carbonate in 20 ml of pyridine there were added 5 ml (0.053 mole) of acetanhydride and it was kept for 45 minutes at ambient temperature. The reaction was stopped by the addition of ice and the product was isolated by the extraction with chloroform at a pH of 8.8 as indicated in Example 2. The chloroform was evaporated and the resinous residue was dissolved in a small amount of ether and filtered. The addition of n-hexane and cooling on an ice-bath resulted in the crystallization of 2'-monoacetate. Yield: 0.64 g (60.7%).

M.p.=153°–158° C.

IR(CHCl₃): 1805 cm⁻¹ (C=O carbonate), 1740 cm⁻¹ (C=O ester, lactone), 1240 cm⁻¹ (—C—O— acetate)

¹H NMR(CDCl₃): 3.3 (3H)s, 2.28 (6H)s, 2.21 (3H)s and 2.05 (3H)s ppm.

EXAMPLE 9

2',4''-diacetyl-N-methyl-11-aza-10-deoxo-10-dihydro erythromycin A 13,14-cyclic carbonate To a solution of 0.7 g (0.0009 mole) of N-methyl-11-aza-10-deoxo-10-dihydro erythromycin A 13,14-cyclic carbonate in 20 ml of pyridine there were added 5 ml (0.053 mole) of acetanhydride and it was kept for 72 hours at ambient temperature. The reaction was stopped by the addition of ice and the product was isolated by the extraction with chloroform at pH 8.4 as indicated in Example 2. After the evaporation of the solvent and the drying of the obtained product with benzene, the resinous residue was suspended in 10 ml of ether while cooling and stirring. The insoluble 2',4''-diacetate was filtered and repeatedly washed with cold ether. Yield: 0.4 g (51.7%).

M.p.=150°–154° C.

¹H NMR(CDCl₃): 3.31 (3H)s, 2.3 (6H)s, 2.2 (3H)s, 2.1 (3H)s and 2.04 (3H)s ppm.

EXAMPLE 10

2'-propionyl-N-methyl-11-aza-10-deoxo-10-dihydro erythromycin A 13,14-cyclic carbonate To a solution of 0.7 g (0.0009 mole) of N-methyl-11-aza-10-deoxo-10-dihydro erythromycin A 13,14-cyclic carbonate in 20 ml of pyridine there were added 10 ml (0.078 mole) of propionic acid anhydride and kept for 1 hour at ambient temperature. The crude 2'-monopropionate was isolated as indicated in Example 2. The chloroform was evaporated and the oily residue was purified by crystallization from ether with n-hexane. Yield: 0.44 g (58.6%).

M.p.=152°–154° C.

IR(CHCl₃): 1805 cm⁻¹(C=O carbonate), 1740 cm⁻¹ (C=O ester, lactone) and 1180 cm⁻¹ (—C—O— propionate).

EXAMPLE 11

2',4''-dipropionyl-N-methyl-11-aza-10-deoxo-10-dihydro erythromycin A 13,14-cyclic carbonate To a solution of 0.75 g (0.00097 mole) of N-methyl-11-aza-10-deoxo-10-dihydro erythromycin A 13,14-cyclic carbonate in 20 ml of pyridine there were added 20 ml (0.155 mole) of propionic acid anhydride and it was kept for 72 hours at ambient temperature. The reaction was stopped by the addition of ice and the product was isolated as indicated in Example 2. The chloroform was evaporated and the residual product was suspended while cooling in dry ether and filtered (benzene:chloroform:methanol=40:55:5, $NH_3$ atmosphere), yielding chromatographically pure 2',4''-dipropionate, m.p. 207°–208° C. Yield: 0.54 g (62.9%).

IR($CHCl_3$): 1805 $cm^{-1}$ (C=O carbonate), 1740 $cm^{-1}$ (C=O ester, lactone) and 1180 $cm^{-1}$ (propionate).

What is claimed is:
1. N-methyl-11-aza-10-deoxo-10-dihydro erythromycin A.

* * * * *

UNITED STATES PATENT AND TRADEMARK OFFICE

CERTIFICATE EXTENDING PATENT TERM
UNDER 35 U.S.C. § 156

PATENT NO.: 4,517,359

DATED: May 14, 1985

INVENTORS: Gabrijela Kobrehel et al.

PATENT OWNER: Pliva Pharmaceutical, Chemical, Food and Cosmetic Industry

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,267 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks